United States Patent [19]
Duich

[11] Patent Number: 5,969,216
[45] Date of Patent: Oct. 19, 1999

[54] CREEPING BENTGRASS *AGROSTIS PALUSTRIS* (*STOLONIFERA*) VARIETY NAMED 'PENN G-1'

[75] Inventor: Joseph M. Duich, State College, Pa.

[73] Assignee: Pennsylvania State University, University Park, Pa.

[21] Appl. No.: 08/926,070

[22] Filed: Sep. 9, 1997

[51] Int. Cl.⁶ .................................. A01H 4/00; A01H 5/00
[52] U.S. Cl. ........................... 800/298; 800/320; 800/295
[58] Field of Search ...................................... 800/200, 250, 800/DIG. 55, 295, 298, 320; 47/58

*Primary Examiner*—Gary Benzion
*Assistant Examiner*—Thomas Haas
*Attorney, Agent, or Firm*—Rothwell, Figg, Ernst & Kurz

[57] ABSTRACT

An *Agrostis palustris* (*stolonifera*) turfgrass variety is disclosed. The invention relates to the seeds, the plants, and to methods of producing an Agrostis plant having the characteristic of average leaf blade width of less than one mm wide.

10 Claims, No Drawings

CREEPING BENTGRASS *AGROSTIS PALUSTRIS* (*STOLONIFERA*) VARIETY NAMED 'PENN G-1'

This invention relates to a novel creeping bentgrass (*Agrostis palustris* (*stolonifera*)), a variety used primarily as commercial golf course turf.

BACKGROUND

There are over 100 species of Bentgrass (Agrostis) but only two are used to any great extent as golf course turf. Bentgrass is well adapted to close mowing due to its prostrate growth habit. They grow best in moist uncompacted soils and have broad temperature hardiness.

Creeping bentgrass (*Agrostis palustris*) is so named due to its ability to creep laterally by stolons. The stolons are able to root at the nodes producing a new plant. Creeping bentgrass is the plant of choice for fairways, tees and greens where the height of cut is below one-half inch.

Creeping bentgrass (*Agrostis palustris*) is a perennial cool season grass that forms a dense mat. The grass spreads by profuse creeping stolons and basal tillers and possesses rather vigorous, shallow roots. Stems, or stolons, are decumbent (creeping) and slender and produce long narrow leaves. Leaf blades are smooth on the upper surface and ridged on the underside, are approximately 1 to 3 mm wide and bluish green in appearance. The ligule is long, membranous, finely toothed or entire and rounded, auricles are absent.

Developing new grass species is difficult, time consuming, and expensive. The developer must sift through thousands of prospective grasses listed in botanical literature, identify promising grasses, and often travel thousands of miles to locate, isolate, identify, transport, quarantine, grow, test, and breed these grasses. This process can take more than 10 years to develop acceptable cultivars. Furthermore, as it turns out, most prospective grasses in nature have no commercial turf value, due to their inability to generate an acceptable ground cover when mowed. The vast majority of natural grasses cannot produce a plush lawn under continuing defoliation.

Yet another complexity facing the plant developer is the unresponsiveness of many wild grasses to plant breeding. The vast majority of wildland grasses lack genetic potential for refinement into desirable turfgrass cultivars. Only after considerable investment in collection and breeding does the developer discover which grass species can be successful bred and which cannot.

The Agrostis genus—better known as the bentgrasses—is comprised of over 100 species, several of which have been developed into successful turfgrasses. One Agrostis in particular, *A. stolonifera* or creeping bentgrass, has become the preeminent grass for golf course putting greens the world over. Another Agrostis species, colonial bentgrass (*A. tenuis* Sibth.), has been bred into a golf course grass useful on tees and fairways in cooler regions. Two or three other Agrostis species find minor turf application, mostly for golf, tennis courts, bowling greens, or an occasional home lawn.

The Agrostis genus is widely distributed throughout the world with representative species found on all of the northern continents. However, of the present-day bentgrass species in use as turfgrasses, all originated from Europe. The original seed of these plants was brought to the US during colonial times.

America has an abundance of native bentgrass species (A. S. Hitchcock, 1951, Manual of the grasses of the United States. USDA Misc. Publ. 200) but none are commercially useable as turf grass.

*Agrostis palustris* (*stolonifera*) is found in nature throughout the mountains of New Mexico, Arizona, and California, along the Rockies, and north to Fairbanks, Ak. Commercial bentgrass species (creeping bentgrass, colonial bentgrass, etc.) all possess stolons (above-ground running stems) and/or rhizomes (below ground running stems). Hitchcock describes *Agrostis palustris* (*stolonifera*) as follows:

Culms slender, tufted, 10 to 30 cm tall, leaves mostly basal, the blades narrow; panicle loosely spreading, 5 to 10 cm long, the branches capillary, flexuous, minutely scabrous; spikelets 1.5 to 2.5 mm long; lemma about 1.3 mm long, awnless; palea minute. Differs from *A. scabra* in the smaller spikelets and in the narrower panicle with shorter flexuous branches.

Piper and Beattie (Charles V. Piper and R. Kent Beattie, 1914, Flora of Southeastern Washington and adjacent Idaho, New Era Printing Co., Lancaster, Pa.) studied the natural occurrence of *Agrostis palustris* (*stolonifera*). They found it common to the alpine woods of the Craig Mountains. Their botanical description is as follows:

Delicate, loosely-tufted, glabrous, perennial, 10–30 cm high; blades flat, narrow, 1–6 cm long; panicle loose, green or purple, 5–10 cm long; rays capillary; spikelets about 1.5 mm long; lower glume scabrous on the keel, slightly larger than the upper; lemma truncate, awnless, 1 mm long; palea minute.

Correll and Correll (D. S. Correll and H. B. Correll, 1972, Aquatic and wetland plants of the Southwestern United States, Stanford Univ. Press, Stanford, Calif.) reported that *Agrostis palustris* (*stolonifera*) is an important native wetland species in moist mountain meadows, swamps, shallow water of ponds, lakes, along streams, and on sand-gravel bars in river beds throughout the West. DeBenedetti and Parsons (S. H. DeBenedetti and D. J. Parsons, 1984, Postfire succession in a Sierran subalpine meadow, Amer. Midland Naturalist 111:118–125) concluded that *Agrostis palustris* (*stolonifera*) was the most important native grass species present in post-fire succession of subalpine grasslands in California. Its tenacious growth under adverse conditions makes it a valuable forage for wildlife.

SUMMARY OF THE INVENTION

The present invention provides for the development of a novel cultivar of bentgrass species never before exploited for turf purposes. Cultivars developed from this species demonstrate extremely dense and fine textured turfgrass properties, including improvements in disease tolerance, fineness of leaf, low height of cut, drought and heat tolerance, deeper rooting and overall turfgrass quality. More specifically, the present invention relates to an *Agrostis palustris* (*stolonifera*) plant having the characteristics of an average leaf blade width of less than 1 mm under turf putting green-maintained conditions.

DEFINITIONS

In the description and tables which follow, a number of terms are used. In order to provide a clear and consistent understanding of the specification and claims, including the scope to be given such terms, the following definitions are provided for either mature plants or in putting green turf plots:

Average leaf blade width: As used herein, the term average leaf blade width means the leaf blade width as measured in millimeters and is determined as follows: Turf plots are grown and maintained in the manner described for evaluation of turf quality. After one year of growth and maintenance, sections of sod 3.08 cm by 12.7 cm are cut and removed from the plot by randomly selecting a representative surface area. Four plugs are removed per plot. Blade width of the second and third youngest subtended leaves per tiller (vertical shoot) are measured on all plants in the sample plug. The youngest leaf occurs at the top of the tiller, with older ones successively down the shoot. The leaf blade width is measured in millimeters across the widest part of the blade, with any creasing of the blade pressed out.

Average shoot density: As used herein, the term average shoot density means the number of grass shoots measured in four plugs. During the process of blade width measurement, the number of grass shoots for each genotype are counted in the plugs. A grass shoot is defined as an autonomous unit possessing a vertical sheath segment, and a minimum of two leaves, including the vertical or bud leaf. Shoot counts per plug are converted numerically into shoots per $dm^2$, based on the exact measured area of the plug.

Bottom Whorl Branches: The term bottom whorl branches means verticullate having three or more branches at the same point on the bottom of the inflourescence.

Brown patch: The term brown patch means the level of disease on the plants. Brown patch is a foliar plant disease incited by the *Rhizoctonia solani* fungus. Brown patch severity is evaluated visually on a 1 to 9 integer rating scale, in a manner similar to turfgrass quality. Symptoms are evaluated during a naturally occurring field disease epidemic. With brown patch evaluation, a rating of 1 would indicate complete necrosis from the disease, 5 would be moderate damage, and 9 would be complete resistance to the disease. Ratings are taken when the turf is actively growing, when regular mowing is taking place, and when no stresses such as drought or other diseases are apparent.

Density: The term density refers to the number of tillers per square decimeter.

Dollarspot: The term dollarspot refers to the disease *Sclerotinia homeocarpa*.

Flag Leaf Length and Width: Flag leaf length and width are the dimensions of the first leaf below the seed head (inflourescence).

Head Count: The term head count refers to the number of seed heads per unit area or per plant.

Leaf color: The term leaf color means that the leaf color is evaluated visually on a 1 to 9 integer rating scale, in a manner similar to turfgrass quality. With leaf color evaluation, a rating of 1 would equate to yellow-green turf, 5 to average green turf, and 9 to intensely dark green turf color. Ratings are taken when the turf is actively growing, when regular mowing is taking place, and when no stresses such as drought or disease are apparent.

Leaf texture: The term leaf texture means that the leaf texture is evaluated visually on a 1 to 9 integer rating scale, in a manner similar to turfgrass quality. With leaf texture evaluation, a rating of 1 would equate to coarse, broad-bladed turf, 5 to turf of an average blade width and 9 to turf of extremely fine blade width. Ratings are taken when the turf is actively growing, when regular mowing is taking place, and when no stresses such as drought or disease are apparent.

Moss: The term moss refers to a Bryophyte contaminant in turf.

Net blotch: The term net blotch disease is incited by the Drechslera/Bipolaris spp. fungi. Net blotch severity is evaluated visually on a 1 to 9 integer rating scale, in a manner similar to turfgrass quality. Symptoms are evaluated during a naturally occurring field disease epidemic. With net blotch evaluation, a rating of 1 would indicate complete necrosis from the disease, 5 would be moderate damage, and 9 would be complete resistance to the disease. Ratings are taken when the turf is actively growing, when regular mowing is taking place, and when no stresses such as drought or other diseases are apparent.

Panicle Length: The term panicle length means the distance from the lowest branch to the tip of the inflourescence.

Plant Height: The term plant height is the distance from the soil surface to the tip of the inflourescence.

Pythium blight: The term Pythium blight refers to the disease incited by Pythium spp.

Seedling vigor: the term seedling vigor means the level of emergence and vigor expressed by the seedlings. Seedling vigor is evaluated visually on a 1 to 9 integer rating scale, in a manner similar to turfgrass quality. With seedling vigor evaluation, ratings are taken 4 weeks after seed establishment, approximately 14 days from the date when the first seedlings are observed protruding above the soil surface. A rating value of 1 would equate to the complete lack of seedling emergence, 5 would indicate an average emergence value, and 9 would indicate extremely vigorous seedling establishment—essentially a complete ground coverage by the turf. Ratings are taken when the turf is actively growing, when no stresses such as drought or disease are apparent. It is assessed just prior to the stand's first mowing.

Snow Mold: As used herein, the term snow mold refers to the disease *Fusarium nivale* (Pink Snow Mold).

Putting green turfgrass quality: As used herein, the term putting green turfgrass quality means that to evaluate turfgrass quality, grasses are seeded into plots 4 by 6 feet or larger, at a seeding rate of 5 grams per $m^2$ (seed grams per square meter) equal to commercial rates listed in turf textbooks. Plots are maintained under fertilization and watering to minimize stress, and 6–7 times weekly mowings at 3 to 5 mm height of cut plus aerated and topdressed as necessary. Three plots of Variety A are planted in a randomized complete block design arrangement with three plots of Variety B, C, D, etc. Visual ratings are taken monthly during the growing season on a 1 to 9 rating scale, with 1 equal to bare ground, 2 equal to thin, brown turf, 3 equal to substandard turf, 4 equal to marginally acceptable turf, 5 equal to average turf, 6 equal to slightly above average turf, 7 equal to dense, robust turf, 8 equal to turf of exception recorded and 9 is equal to ideal turf quality. Ratings are conducted by a university-trained specialist with a graduate degree in Turfgrass Science. Monthly data ratings are analyzed using a statistical procedure known as the analysis of variance or t-test at the 0.05 level of probability. A significant analysis indicates the two varieties, A and B, are different, and that the difference is not due to random error or natural plant and soil variability. A non-significant analysis would indicate that the varieties A and B were indistinguishable in turf quality or mature plant parameters.

Vegetative propagules: As used herein, the term vegetative propagules means sprigs, plugs, stolons and sod.

DETAILED DESCRIPTION OF THE INVENTION

The variety PENN G-1 (experimental designation PSU G-1) is based on a single segregated plant selected on the Par-3 course from the Augusta National Golf Club, Augusta, Ga. in 1984. Eight similar types were selected from two greens originally seeded to Penneagle bent and overseeded with Penncross.

The selections were based on a dense upright growth habit, very fine leaf texture, minimum spiking from golf shoes and ability to spread as segregates compared to the greens bent population, thereby, attracting attention. These selections were designated in the breeding program as the "G: series in contrast to the "A" series from the main course which were selected with similar criteria.

Both G and A series selections were cloned, pot planted and induced to flower in a growth chamber. Isolated crossing blocks were established in the greenhouse from which 250 plants each were nursery space planted in isolated field blocks.

The first cycle of reselection consisted of chemically roguing all but 30–50 plants of each sibline based on vegetative and flowering stage appearance prior to anthesis. Three lines were eliminated due to degree of segregation. Re-selected clones were pot planted and again induced to flower in a growth chamber to save a reproductive year, and placed in isolated greenhouse crossing blocks. Following seed harvest, 300 seedlings were field planted for the next reselection cycle. Seed from the first cycle plants was used to establish a pilot putting green turf planting to conform the fine texture and dense qualities of the original parents.

The second cycle of reselection consisted of 40–50 plants of each experimental lines of both the G and A series. Selected clones were sent to Oregon for seed set and any further reselection under production state conditions. Clones of each line were replicated and isolated planted. The G series now consisted of G-1, G-2, and G-6 and were further reselected to 20–30 replicated plants each in Oregon. These clones constitute breeder planting stock and the first generation seed used for seed yield trials and subsequently certified seed production.

Due to inherent heterogeneity of this tetraploid species, production of G-1 and associated cultivars shall be limited to a two generatation system, breeders and certified to maintain optimum stability. Uniformity and stability of PENN G-1 was ascertained by inspection of seed yield plantings in both and reproductive stages of growth. The variants in PENN G-1 as well as G-2, G-6, A-1, A-2 and A-4 were quite similar. The normal growth habit is semi-erect with variants in the vegetative stage consisting of a few more spreading decumbent or semi-decumbent types, and non-spreading fine-leaved "ball types." In the reproductive stage, the low types produce decumbent seed heads that protrude laterally at plant perimeter with no heads arising from the center of plants. The fine and very dense ball nonspreading ball types produce either few or no flowers. These variants are estimated to constitute approximately 0.5% of the total population.

A PVP nursery was established at the Pure Seed Testing Research Farm in Hubbard, Oregon in 1995 consisting of 20 creeping bent cultivars with four replications of 25 space plants each including new Penn State varietal releases Penn A-1, Penn A-2, Penn A-4, Penn G-1, Penn G-2, Penn G-6, Seaside II and 12 commercial bents.

Morphological character measurements are shown in Table 1 and visual rating to the closest 10% by three individual raters in Table 2. From Table 2, character ratings with a minimum of 20% difference were used to separate varieties.

Penn G-1 significantly differed from other bent variety characteristics as follows:

Penn G-2: Flagleaf length, flagleaf width, head count, leaf anthocyanin, and ligule shape.

Penn G-6: Flagleaf width, leaf anthocyanin, ligule shape, ligule margin, panicle type, panicle anthocyanin, branches at anthesis and fruit.

Penn A-1: Panicle length, flagleaf width, leaf anthocyanin, ligule shape, panicle type and panicle anthocyanin.

Penn A-2: Panicle length, number of bottom whorls, head count, leaf anthocyanin, ligule shape, panicle anthocyanin, branches at anthesis and branch surface.

Penn A4: Flagleaf width, leaf anthocyanin, ligule shape, ligule pubescence, ligule margin, panicle anthocyanin and branches at anthesis.

Seaside II: Flagleaf width, leaf anthocyanin, ligule shape, panicle type, panicle anthesis, branches at anthesis and fruit and the branch surface.

Seaside: Panicle length, leaf anthocyanin, ligule shape, ligule margin and panicle type.

Southshore: Panicle length, flagleaf length and flagleaf width.

Crenshaw: Flagleaf length, flagleaf width, number of panicle bottom whorls and head count.

Providence: Panicle length, flagleaf length and flagleaf width.

Regent: Panicle length and head count.

Putter: Panicle length and head count.

Lopez: Panicle length, flagleaf length and width, number of panicle bottom whorls and plant count.

SR-1020: Panicle length, flagleaf length and width.

ProCup: Panicle length, flagleaf width, number of panicle bottom whorls and head count.

Penncross: Panicle length, flagleaf length and width and head count.

Cato: Flagleaf width.

Pennlinks: Plant height, panicle length and flagleaf length and width.

Based on space plant morphology Penn G-1 is most similar to Cato but is further differentiated in characteristics under close cut turf conditions as shown in Tables 3 and 4 for leaf texture and density.

In a close height of cut managed at 3.2 mm, PENN G-1 creeping bent is unique in producing a very fine and dense putting green turf. Measured leaf textures in three locations show a significantly narrow blade width ranging from 0.65 to 0.72mm as shown in Table 3.

Unique high density stands under putting green management are supported by measured turf shoot densities ranging from 1996 to 2612 per square decimeter compared to 765 to 1509 for commercial bents in Augusta, Ga. and Turin, Italy as shown in Table 4, and visual ratings shown in Tables 5, 6, and 7. Superior turf quality performance is illustrated in evaluations for three locations shown in Tables 8, 9 and 10 and resistance to moss invasions is shown in Table 11. PENN G-1 also shows only a slight amount of winter purple coloring under frosting conditions in Georgia as shown in Table 12.

Although more limited in turf testing than co-developed varieties due to a contamination of seed supply, PENN G-1 showed good resistance to brownpatch and leafspot and moderate susceptibility to snowmold, dollarspot and pythium as shown in Tables 5, 7 and 13.

1. Species: Creeping Bentgrass (*Agrostis palustris*)
2. Adaptation: Northeast - Adapted
   Southeast - Adapted
   North Central - Adapted
   Pacific Northwest - Adapted
3. Maturity: (At first anthesis)
   3 days earlier than Penncross
   2 days later than Pennlinks
4. Height: (Average of longest 10 shoots from soil surface to top of head)
   Height at maturity: 53 cm
   10 cm shorter than Seaside
   Same as Providence
   10 cm taller than Penncross
5. Growth Habit: 1% Decumbent
   99% Geniculate
6. Vegetative Reproduction:
   Rhizomes: Absent
   Stolons: Present - 100% Stolons
7. Leaf Blade: Texture (fineness): Very fine (Kingstown)
   Width (Flag leaves): 48 mm
   Length: (Flag Leaves): 92 cm
8. Leaf Sheath: Anthocyanin: Present
   Red Sheaths: 100%
9. Ligule: (Lower and Middle Leaves):
   Shape at Apex: Acute - 50% Rounded - 20% Truncate - 30%
   Pubescence: Glabrous - 100%
   Margins: Entire - 20% Toothed - 80%
10. Lemma:
    Shape: 100% Lanceolate
    Color: 100% Silvery
    Texture: 100% Smooth
    Pubescence: 100% Glabrous
    Basal Hairs: 100% Absent
    Awns: 100% Absent
    Width: 39 mm     Length (exclusive of awn): 15 mm
11. Panicle:
    Type (in anthesis): 20% Open     80% Compact
    Anthocyanin: 80% Absent     20% Present
    Branches (in anthesis): 90% Appressed     10% Ascending
    Branches (in fruit): 90% Appressed     10% Ascending
    Branch Surface: 90% Smooth     10% Scabrous
12. Seed:
    .076 grams per 1000 seed
13. Spring Green Up:
    Medium (Astoria)
14. Environmental Resistance:
    Cold: Resistant
    Heat: Resistant
15. Disease Resistance:
    Red Leaf Spot - *Drechslera erythrospila*: Resistant
    Pythium Blight - *P. Aphanidermatum*: Susceptible
    Fusarium Patch - Pink Snow Mold (*F. Nivale*): Susceptible
    Dollar Spot (*Sclerotinia homoeocarpa*): Susceptible
    Pythium Blight (*P. Ultimum*): Susceptible
    Brown Patch (*Rhizoctonia solani*): Resistant
16. Variety That Most Closely Resembles Submitted Variety:
    (Degree of resemblance is rated as follows: 1 = Submitted variety is less than, lighter, or inferior to similar variety, 2 = Same as, 3 = More than, darker or superior.)
    Growth Habit: Pennlinks - 2
    Cold Resistance: Pennlinks - 2
    Brown Patch: Pennlinks - 3
    Leaf color: Pennlinks - 2
    Panicle Type: Pennlinks - 2
    Turf Fineness: Pennlinks - 3
    Heat Resistance: Pennlinks - 2
    Moss Resistance: Pennlinks - 3

TABLES

The tables listed below show comparisons with the instant invention and other known bentgrass cultivars.

Table 1 shows the measurements for plant height, panicle length, flag leaf length, flag leaf width, bottom whorl branches and head count.

Table 2 shows morphological characteristics for leaf sheath anthocyanin, ligule shape, ligule pubescence, ligule margins, panicle type, panicle anthocyanin, branches in anthesis, branches in fruit, and branch surface.

Table 3 shows the leaf texture of bentgrass cultivars maintained as putting green turf in University Park, Pennsylvania, Augusta, Ga. and Turin, Italy.

Table 4 shows the shoot density in Augusta, Ga. and Turin Italy.

Table 5 shows the density evaluations for 1992, 1993 and 1994 and disease statistics for Dollarspot and Snowmold.

Table 6 is a 1991 evaluation for density, texture, growth habit, leafspot and brownpatch using a scale of 1 to 9 with 9 being best.

Table 7 is a density evaluation and disease statistics for Pythium at Loxahatchee Country Club in West Palm Beach, Fla. These figures use a scale of 1 to 9 with 9 being best.

Table 8 shows quality ratings at Augusta National Golf Club from 1992 to 1995.

Table 9 indicates the seasonal turf quality in winter, spring, summer and fall, 1992 at the Turf Seed Research at Rolesville, N.C. These figures use a scale of 1 to 9 with 9 being best.

Table 10 is the mean annual turf quality at Turin, Italy for 1992, 1993 and 1994 also using the scale of 1 to 9 with 9 being best.

Table 11 is the percent of moss present in Turin, Italy during 1993 and 1994.

Table 12 shows winter purple color ratings at Augusta National Golf Club, Georgia in 1993–1994.

Table 13 shows mean Rhizoctonia brownpatch ratings for 1992 in Rolesville, N.C.

TABLE 1

Morphological Character Measurements

| Plant Height (cm) | | Panicle Length (cm) | | Flag Leaf Length (cm) | | Flag Leaf Width (mm) | | # Bottom Whorl Branches | | Head Count | |
|---|---|---|---|---|---|---|---|---|---|---|---|
| Seaside II | 63.8 | Penn A-1 | 13.1 | Penn G-1 | 9.25 | Providence | 4.82 | Penn A-1 | 7.3 | Seaside | 373 |
| Seaside | 63.1 | Seaside | 13.0 | Seaside II | 9.03 | Seaside II | 4.57 | Penn A-2 | 7.0 | Providence | 370 |
| Penn A-1 | 62.5 | Southshore | 12.8 | Seaside | 8.90 | Lopez | 4.53 | Procup | 7.0 | Penn G-1 | 264 |
| Southshore | 60.2 | Crenshaw | 12.3 | Regent | 8.47 | Crenshaw | 4.52 | Crenshaw | 6.7 | Seaside II | 22 |
| Penn G-2 | 57.1 | Cato | 12.2 | Procup | 8.26 | Penn A-1 | 4.45 | Lopez | 6.6 | Cato | 213 |
| Crenshaw | 54.1 | Penn G-1 | 11.7 | Penn A-1 | 7.98 | Cato | 4.40 | Putter | 6.4 | Penn A-1 | 193 |
| Providence | 53.1 | Penn G-6 | 11.7 | Putter | 7.91 | Procup | 4.37 | VNS | 6.4 | Penn AA | 181 |
| Penn G-1 | 53.0 | Seaside II | 11.6 | Penn G-6 | 7.82 | Penncross | 4.32 | Pennlinks | 6.4 | Pennlinks | 178 |
| Penn A-2 | 52.2 | Penn A-4 | 11.6 | Cato | 7.78 | Penn G-6 | 4.17 | Penn G-6 | 6.3 | Southshore | 170 |
| Regent | 51.4 | Penn G-2 | 11.4 | Penn A-2 | 7.73 | Southshore | 4.17 | Penncross | 6.3 | SR 1020 | 154 |
| Putter | 49.9 | Putter | 11.2 | Crenshaw | 7.48 | Penn G-2 | 3.95 | Providence | 6.3 | Penn G-6 | 153 |
| Lopez | 47.5 | Pennlinks | 11.0 | Penn G-2 | 7.43 | Pennlinks | 3.83 | 5R1020 | 6.0 | Crenshaw | 133 |
| Penn AA | 46.7 | Regent | 11.0 | Lopez | 7.13 | SR 1020 | 3.82 | Cato | 5.8 | VNS | 132 |
| VNS | 46.0 | VNS | 11.0 | Penncross | 7.06 | Penn A-4 | 3.77 | Penn G-2 | 5.6 | Penn G-2 | 129 |
| 5R1020 | 44.3 | Procup | 10.8 | Southshore | 7.06 | Putter | 3.75 | Regent | 5.6 | Regent | 123 |
| Procup | 44.3 | Lopez | 10.5 | VNS | 6.87 | VNS | 3.62 | Penn G-1 | 5.6 | Penncross | 10 |
| Penn G-6 | 43.2 | Providence | 10.2 | SR 1020 | 6.86 | Seaside | 3.43 | Southshore | 5.5 | Putter | 100 |
| Penncross | 43.2 | SR 1020 | 10.0 | Providence | 6.68 | Penn G-1 | 2.83 | Seaside II | 5.4 | Penn A-2 | 95 |
| Cato | 42.3 | Penncross | 10.0 | Pennlinks | 6.50 | Penn A-2 | 2.58 | Seaside | 4.8 | Lopez | 81 |
| Pennlinks | 37.8 | Penn A-2 | 9.9 | Penn AA | 5.90 | Regent | 2.38 | Penn AA | 4.6 | Procup | 59 |
| LSD | 13.8 | | 0.6 | | 1.56 | | 0.96 | | 0.9 | | 119 |

TABLE 2

Morphological Characteristics

| | Seaside | Seaside II | Penn A-1 | Penn A-2 | Penn A-4 | Penn G-1 | Penn G-2 | Penn G-6 |
|---|---|---|---|---|---|---|---|---|
| Leaf sheath anthocyanin | | | | | | | | |
| Present | 40 | 0 | 0 | 0 | 0 | 100 | 0 | 0 |
| Absent | 60 | 100 | 100 | 100 | 100 | 0 | 100 | 100 |
| Ligule shape | | | | | | | | |
| Acute | 20 | 60 | 80 | 20 | 10 | 30 | 20 | 100 |
| Truncate | 60 | 40 | 20 | 80 | 90 | 30 | 80 | 0 |
| Round | 20 | 0 | 0 | 0 | 0 | 20 | 0 | 0 |
| Ligule pubescence | | | | | | | | |
| Glabrous | 100 | 100 | 100 | 100 | 0 | 100 | 100 | 90 |
| Pubescence | 0 | 0 | 0 | 0 | 100 | 0 | 0 | 10 |
| Ligule margins | | | | | | | | |
| Entire | 50 | 30 | 30 | 20 | 100 | 20 | 20 | 90 |
| Toothed | 50 | 70 | 70 | 80 | 0 | 80 | 80 | 10 |
| Panicle type | | | | | | | | |
| Open | 40 | 40 | 50 | 30 | 30 | 20 | 30 | 10 |
| Compact | 60 | 60 | 50 | 70 | 70 | 80 | 70 | 90 |
| Panicle anthocyanin | | | | | | | | |
| Present | 0 | 30 | 0 | 70 | 0 | 20 | 30 | 90 |
| Absent | 100 | 70 | 100 | 30 | 100 | 80 | 70 | 10 |

TABLE 2-continued

Morphological Characteristics

|  | Seaside | Seaside II | Penn A-1 | Penn A-2 | Penn A-4 | Penn G-1 | Penn G-2 | Penn G-6 |
|---|---|---|---|---|---|---|---|---|
| Branches in anthesis | | | | | | | | |
| Appressed | 80 | 70 | 80 | 70 | 60 | 90 | 80 | 100 |
| Ascending | 10 | 30 | 20 | 30 | 40 | 10 | 20 | 0 |
| Spreading | 10 | 0 | 0 | 0 | 0 | 0 | 0 | 0 |
| Branches in fruit | | | | | | | | |
| Appressed | 90 | 50 | 80 | 70 | 80 | 90 | 80 | 100 |
| Ascending | 5 | 50 | 20 | 30 | 20 | 10 | 20 | 0 |
| Spreading | 5 | 0 | 0 | 0 | 0 | 0 | 0 | 0 |
| Branch surface | | | | | | | | |
| Smooth | 90 | 70 | 90 | 100 | 90 | 90 | 80 | 90 |
| Scabrous | 10 | 30 | 10 | 0 | 10 | 10 | 20 | 10 |

TABLE 3

Leaf texture of bentgrass cultivars maintained as putting green turf in three locations (mm)

| University Park, PA | | Augusta, GA | | Turin, Italy | |
|---|---|---|---|---|---|
| Penn G-2 | 0.61 | Penn A-2 | 0.63 | Penn G-2 | 0.63 |
| Penn G-6 | 0.63 | Penn A-1 | 0.65 | Penn G-6 | 0.70 |
| Penn A-1 | 0.63 | Penn G-2 | 0.65 | Penn A-1 | 0.70 |
| FHG-1 | 0.63 | Penn G-1 | 0.68 | Penn G-1 | 0.72 |
| Penn G-1 | 0.65 | Penn A-4 | 0.69 | Seaside II | 0.79 |
| Penn A-2 | 0.67 | Penn G-6 | 0.71 | Pennlinks | 0.80 |
| Penn A-4 | 0.69 | Crenshaw | 0.79 | SR 1020 | 0.80 |
| Seaside II | 0.74 | Cato | 0.80 | Southshore | 0.84 |
| Pennlinks | 0.77 | Seaside II | 0.80 | Penncross | 0.85 |
| SR 1020 | 0.80 | Penncross | 0.99 | Providence | 0.85 |
| Providence | 0.81 | | | Putter | 0.86 |
| Penneagle | 0.85 | | | Cobra | 0.88 |
| Putter | 0.89 | | | National | 0.90 |
| Carmen | 0.93 | | | Seaside | 0.90 |
| Cobra | 0.95 | | | Penneagle | 0.95 |
| Penncross | 0.99 | | | Emerald | 0.96 |
| Emerald | 1.12 | | | | |
| LSD (.05) | 0.04 | | 0.06 | | 0.10 |

TABLE 4

Bentgrass shoot density/dm² Augusta, GA and Turin, Italy

| | Augusta, GA | | | Turin, Italy | |
|---|---|---|---|---|---|
| | 1992 | 1993 | | 1992 | 1993 |
| Penn A-2 | 2376 | 2392 | Penn G-1 | 1574 | 2612 |
| Penn A-1 | 1815 | 2145 | Penn G-2 | 1080 | 2546 |
| Penn G-1 | 1881 | 1996 | Penn G-6 | 1065 | 2378 |
| Penn G-2 | 2079 | 1963 | Penn A-1 | 1075 | 2240 |
| Penn A-4 | 1617 | 1917 | Seaside II | 1043 | 2058 |
| Penn G-6 | 1683 | 1838 | Southshore | — | 1509 |
| Crenshaw | 1617 | 1419 | Pennlinks | 1000 | 1504 |
| Cato | 1254 | 1287 | Providence | 914 | 1425 |
| Penncross | 1122 | 1270 | SR 1020 | 1017 | 1419 |
| Seaside II | 1419 | 1056 | Putter | 1091 | 1272 |
| | | | Penneagle | 980 | 1241 |
| | | | Cobra | 1170 | 1196 |
| | | | National | 908 | 1013 |
| | | | Emerald | 915 | 1010 |
| | | | Seaside | 591 | 765 |
| LSD (.05) | 180 | 214 | | 258 | 178 |

TABLE 5

1992–94 Density Evaluations, 1992 Dollarspot and 1994–95 Snowmold—Penn State University

| | Density | | | Dollarspot | |
|---|---|---|---|---|---|
| | 1992 | 1993 | 1994 | sq. Ft. | Snowmold |
| PSU G-2 | 8.9 | 8.5 | 8.5 | 1.7 | 5.7 |
| PSU A-4 | 8.7 | 8.3 | 8.4 | 3.7 | 5.7 |
| PSU A-2 | 8.9 | 8.7 | 8.1 | 2.0 | 7.7 |
| PSU 115 | 8.9 | 8.8 | 8.5 | 2.3 | 3.2 |
| PSU A-1 | 8.9 | 8.7 | 8.0 | 0.7 | 5.5 |
| PSU G-6 | 8.4 | 8.7 | 8.3 | 2.7 | 5.5 |
| PSU G-1 | 8.5 | 8.5 | 8.2 | 7.0 | 6.5 |
| PPSU DF-1 | 8.2 | 7.8 | 8.1 | 1.7 | 7.3 |
| Pennlinks | 7.8 | 7.7 | 7.6 | 1.0 | 7.7 |
| Providence | 7.8 | 7.8 | 7.3 | 0.3 | 6.7 |
| 88CBE | 7.7 | 6.7 | 7.7 | 1.7 | 7.3 |
| Cato | 7.5 | 7.8 | 6.5 | 3.0 | 8.2 |
| Crenshaw | 6.8 | 7.8 | 7.0 | 18.7 | 5.3 |
| Regent | 7.8 | 6.7 | 6.7 | 3.0 | 7.5 |
| SR1020 | 7.5 | 7.5 | 7.2 | 7.7 | 6.7 |
| Putter | 7.6 | 6.3 | 6.7 | 5.3 | 7.3 |
| Cobra | 7.0 | 6.7 | 6.5 | 2.0 | 7.3 |
| ProCup | 7.0 | 6.5 | 6.2 | 3.0 | 7.3 |
| Lopez | 7.0 | 6.5 | 6.2 | 3.0 | 6.5 |
| Penncross | 6.0 | 5.0 | 5.2 | 5.7 | 7.3 |
| LSD (0.05) | 1.2 | 1.1 | 1.2 | 1.1 | 2.4 |

TABLE 6

1991 Evaluation for Density, Texture, Growth Habit, Leafspot and Brownpatch (Scale 1 to 9—9 = Best—Penn State University

| | Density | Texture | Growth Habit | Leafspot | Brownpatch |
|---|---|---|---|---|---|
| PSU G-1 | 8.5 | 8.3 | 8.3 | 7.3 | 8.0 |
| PSU G-2 | 8.5 | 8.7 | 8.5 | 8.7 | 8.2 |
| PSU G-3 | 8.6 | 8.3 | 8.5 | 8.7 | 7.7 |
| PSU G-6 | 8.5 | 8.7 | 8.3 | 8.5 | 8.3 |
| PSU A-1 | 8.4 | 8.7 | 8.2 | 7.8 | 7.7 |
| PSU A-2 | 8.6 | 8.3 | 8.5 | 6.2 | 9.0 |
| PSU A-4 | 8.4 | 8.3 | 8.3 | 5.0 | 8.8 |
| PSU DF-1 | 8.6 | 8.3 | 8.5 | 7.3 | 8.0 |
| FH G-1 | 8.4 | 8.7 | 8.2 | 7.8 | 8.7 |
| Pennlinks | 8.0 | 8.0 | 7.7 | 7.5 | 7.0 |
| Penncross | 7.2 | 4.5 | 5.0 | 6.7 | 7.3 |
| Penneagle | 7.6 | 7.3 | 7.7 | 6.7 | 8.3 |
| Providence | 8.0 | 7.7 | 7.7 | 7.8 | 8.2 |
| Carmen | 6.7 | 4.5 | 6.3 | 7.0 | 5.3 |
| Cobra | 6.3 | 4.5 | 7.7 | 7.0 | 8.3 |

TABLE 6-continued

1991 Evaluation for Density, Texture, Growth Habit, Leafspot and Brownpatch (Scale 1 to 9—9 = Best—Penn State University)

|  | Density | Texture | Growth Habit | Leafspot | Brownpatch |
|---|---|---|---|---|---|
| Putter | 7.8 | 5.7 | 7.2 | 6.7 | 7.6 |
| SR 1020 | 8.2 | 7.8 | 8.0 | 7.0 | 7.0 |
| Emerald | 5.7 | 4.0 | 5.0 | 4.0 | 7.1 |
| LSD (0.05) | 1.2 | 0.9 | 1.0 | 2.0 | 2.2 |

TABLE 7

Loxahatchee Country Club, West Palm Beach, Florida 1991 Bent Test

|  | Density 1 to 9—9 = Best | | | | Pythium |
|---|---|---|---|---|---|
|  | 1992 | 1993 | 1994 | Avg | 1992 |
| PSU G-2 | 8.5 | 7.7 | 7.3 | 7.8 | 5.7 |
| PSU A-1 | 7.8 | 7.3 | 7.5 | 7.5 | 5.7 |
| PSU G-6 | 7.3 | 7.6 | 7.6 | 7.5 | 6.0 |
| PSU A-2 | 7.9 | 7.4 | 6.8 | 7.4 | 5.7 |
| PSU A-4 | 6.5 | 7.4 | 7.2 | 7.1 | 5.7 |
| Crenshaw | 7.3 | 6.4 | 6.5 | 6.7 | 4.3 |
| Seaside II | 7.3 | 6.2 | 6.5 | 6.7 | 3.7 |
| PSU G-1 | 8.3 | 7.3 | 6.3 | 6.6 | 5.3 |
| Cato | 6.3 | 5.9 | 6.5 | 6.2 | 5.7 |
| Pennlinks | 5.9 | 6.6 | 5.4 | 6.0 | 6.0 |
| SR 1020 | 5.9 | 6.6 | 5.3 | 6.0 | 4.7 |
| Providence | 5.1 | 6.3 | 5.9 | 5.8 | 7.7 |
| Syn-1 | 4.7 | 4.3 | 5.2 | 4.7 | 4.0 |
| Penncross | 4.4 | 4.6 | 4.5 | 4.5 | 5.3 |
| LSD (.05) | 0.4 | 0.5 | 0.5 | 0.4 |  |

TABLE 8

Augusta National Golf Club 1991 Nursery Test

Quality: 1 to 9.9 = best

|  | 7-92 | 10-92 | 2-93 | 4-93 | 7-93 | 1-94 | 7-94 | 8-94 | 10-94 | 6-95 | Avg |
|---|---|---|---|---|---|---|---|---|---|---|---|
| PSU G-2 | 8.0 | 8.5 | 8.0 | 8.5 | 8.0 | 8.5 | 8.2 | 8.0 | 8.0 | 8.0 | 8.2 |
| PSU A-1 | 7.0 | 8.0 | 8.0 | 8.2 | 8.0 | 8.2 | 8.0 | 8.7 | 8.0 | 8.0 | 8.0 |
| PSU G-1 | 7.0 | 7.0 | 8.2 | 8.2 | 8.2 | 9.0 | 8.5 | 7.7 | 8.2 | 8.2 | 8.0 |
| PSU A-4 | 8.0 | 7.0 | 7.8 | 8.5 | 8.0 | 8.5 | 8.0 | 8.5 | 8.0 | 8.0 | 8.0 |
| PSU A-2 | 7.0 | 8.0 | 8.2 | 8.5 | 8.2 | 7.2 | 7.7 | 8.5 | 8.2 | 8.2 | 8.0 |
| PSU G-6 | 7.0 | 7.5 | 7.5 | 7.7 | 7.5 | 6.0 | 7.5 | 7.5 | 7.8 | 7.8 | 7.4 |
| Cato | 6.0 | 6.0 | 6.5 | 6.5 | 6.5 | 6.2 | 6.0 | 7.0 | 6.5 | 6.5 | 6.4 |
| Crenshaw | 6.0 | 6.0 | 6.5 | 7.0 | 6.5 | 6.0 | 5.5 | 6.7 | 6.0 | 5.5 | 6.2 |
| PSU DF-1 | 6.0 | 6.0 | 6.0 | 5.0 | 4.0 | 6.5 | 5.5 | 6.0 | 5.5 | 5.5 | 5.6 |
| Penncross | 5.0 | 5.0 | 4.0 | 4.5 | 6.0 | 3.0 | 4.5 | 5.0 | 6.0 | 6.5 | 4.9 |

TABLE 9

Seasonal turf quality for 1992
Turf Seed Research, Rolesville, NC

|  | Winter | Spring | Summer | Fall | Average |
|---|---|---|---|---|---|
| PSU G-6 | 5.8 | 5.9 | 8.1 | 8.0 | 7.0 |
| PSU A-2 | 6.1 | 7.0 | 7.9 | 6.7 | 6.9 |
| PSU A-4 | 6.7 | 7.2 | 7.3 | 6.5 | 6.8 |
| PSU A-1 | 4.8 | 6.3 | 8.2 | 7.7 | 6.7 |
| PSU G-2 | 5.4 | 5.9 | 7.8 | 7.2 | 6.6 |
| PSU G-1 | 5.4 | 5.5 | 6.6 | 6.8 | 6.1 |
| Cobra | 6.2 | 6.5 | 5.7 | 5.0 | 6.0 |
| Providence | 5.4 | 5.8 | 6.3 | 5.8 | 5.9 |

TABLE 9-continued

Seasonal turf quality for 1992
Turf Seed Research, Rolesville, NC

|  | Winter | Spring | Summer | Fall | Average |
|---|---|---|---|---|---|
| ProCup | 6.1 | 6.0 | 5.4 | 6.0 | 5.9 |
| PSU DF-1 | 5.5 | 6.4 | 5.6 | 5.7 | 5.8 |
| Penneagle | 5.7 | 6.1 | 5.4 | 5.7 | 5.7 |
| 88 CBE | 5.7 | 6.1 | 5.7 | 5.3 | 5.7 |
| SR 1020 | 6.0 | 6.3 | 5.1 | 5.3 | 5.7 |
| Regent | 5.0 | 5.5 | 6.1 | 5.5 | 5.5 |
| Pennlinks | 4.7 | 5.7 | 5.3 | 5.7 | 5.4 |
| PREF | 4.8 | 5.6 | 4.9 | 5.8 | 5.3 |
| Putter | 5.2 | 5.3 | 5.4 | 5.0 | 5.2 |
| Lopez | 4.4 | 4.7 | 5.8 | 5.5 | 5.1 |
| PREC | 4.7 | 5.2 | 4.7 | 5.5 | 5.0 |
| Penncross | 6.8 | 5.6 | 3.2 | 3.3 | 4.7 |
| LSD (0.05) | 1.1 | 1.2 | 1.1 | 1.2 | 1.2 |

TABLE 10

Mean annual turf quality
Turin, Italy 1992–1994

|  | Quality 1 to 9—9 = Best | | | |
|---|---|---|---|---|
|  | 1992 | 1993 | 1994 | Average |
| Penn G-1 | 7.4 | 7.4 | 6.9 | 7.2 |
| Penn A-1 | 7.3 | 7.3 | 6.6 | 7.1 |
| Penn G-6 | 7.2 | 6.8 | 6.7 | 6.9 |
| Penneagle | 7.0 | 6.4 | 6.4 | 6.6 |
| Providence | 7.0 | 6.2 | 6.2 | 6.5 |
| Penn G-2 | 6.5 | 6.3 | 6.5 | 6.4 |
| Putter | 7.1 | 6.2 | 5.9 | 6.4 |
| Pennlinks | 6.9 | 6.2 | 5.9 | 6.3 |

TABLE 10-continued

Mean annual turf quality
Turin, Italy 1992–1994

|  | Quality 1 to 9—9 = Best | | | |
|---|---|---|---|---|
|  | 1992 | 1993 | 1994 | Average |
| Penncross | 7.0 | 5.7 | 5.8 | 6.2 |
| Southshore | — | 6.5 | 5.5 | 6.0 |
| Cobra | 6.7 | 5.6 | 5.7 | 6.0 |
| Seaside II | 6.4 | 5.8 | 5.5 | 5.9 |
| SR 1020 | 6.7 | 5.3 | 5.2 | 5.7 |
| National | 6.2 | 4.8 | 4.9 | 5.3 |

TABLE 10-continued

Mean annual turf quality
Turin, Italy 1992–1994

Quality 1 to 9—9 = Best

|         | 1992 | 1993 | 1994 | Average |
|---------|------|------|------|---------|
| Emerald | 6.3  | 4.3  | 4.5  | 5.0     |
| Seaside | 4.8  | 3.5  | 3.9  | 4.1     |

TABLE 11

Presence of moss in 1993 and 1994
Turin, Italy

|            | % Moss—1993 | % Moss—1994 |
|------------|-------------|-------------|
| Penn G-1   | 0.10        | 1.93        |
| Penn A-1   | 0.05        | 1.14        |
| Penn G-6   | 0.33        | 3.64        |
| Southshore | 0.72        | 3.67        |
| Penneagle  | 2.55        | 5.19        |
| Penn G-2   | 0.55        | 2.64        |
| Putter     | 3.94        | 6.67        |
| Pennlinks  | 3.19        | 7.19        |
| Providence | 2.86        | 3.00        |
| Penncross  | 3.36        | 12.29       |
| Seaside II | 3.80        | 7.36        |
| Cobra      | 3.58        | 11.19       |
| SR 1020    | 4.08        | 8.67        |
| National   | 11.17       | 18.81       |
| Emerald    | 9.33        | 17.76       |
| Seaside    | 31.67       | 26.78       |
| Astoria    | 24.77       | 35.57       |
| LSD (.05)  | 10.20       | 6.81        |

TABLE 12

Winter purple color ratings
Augusta National Golf Club, Georgia 1993–94

Percent Winter Purple Color

|            | 1993 | 1994 | Avg. |
|------------|------|------|------|
| Penn A-1   | 12   | 3    | 7.5  |
| Penn A-4   | 6    | 10   | 8.0  |
| Penn G-2   | 3    | 15   | 9.0  |
| Penn G-1   | 15   | 5    | 10.0 |
| Penn A-2   | 2    | 20   | 11.0 |
| Seaside II | 10   | 40   | 25.0 |
| Penncross  | 25   | 30   | 27.5 |
| Cato       | 30   | 40   | 35.0 |
| Penn G-6   | 40   | 50   | 45.0 |
| Crenshaw   | 60   | 50   | 55.0 |

TABLE 13

Mean Rhizoctonia brownpatch ratings for 1992
Turf Seed Research, Rolesville, NC
Scale: 1 to 9.9 = best

|         | Average |
|---------|---------|
| PSU A-1 | 8.7     |
| PSU G-6 | 8.3     |

TABLE 13-continued

Mean Rhizoctonia brownpatch ratings for 1992
Turf Seed Research, Rolesville, NC
Scale: 1 to 9.9 = best

|            | Average |
|------------|---------|
| PSU G-1    | 8.0     |
| PSU G-2    | 7.3     |
| PSU A-2    | 6.7     |
| Lopez      | 6.3     |
| Cobra      | 5.3     |
| 88 CBE     | 5.3     |
| Regent     | 5.0     |
| PSU DF-1   | 5.0     |
| Pennlinks  | 4.7     |
| ProCup     | 4.7     |
| PSU A-4    | 4.7     |
| Penneagle  | 4.7     |
| Providence | 4.3     |
| Syn PREF   | 3.7     |
| Putter     | 3.3     |
| Syn PREC   | 3.0     |
| SR 1020    | 2.3     |
| Penncross  | 1.0     |
| LSD (0.05) | 3.8     |

DEPOSIT INFORMATION

*Agrostis palustris* (*stolonifera*) seed of this invention has been placed on deposit with the American Type Culture Collection (ATCC), Manapaar, Va. under Deposit Accession Number 203435 on Nov. 6, 1998.

Although the foregoing invention has been described in some detail by way of illustration and example for purposes of clarity and understanding, it will be obvious that certain changes and modifications may be practiced within the scope of the invention, as limited only by the scope of the appended claims.

What is claimed is:

1. Seed of an *Agrostis palustris* line designated PENN G-1, and having ATCC Accession Number 203435.

2. An *Agrostis palustris* and its parts produced by the seed of claim 1 and its plant parts.

3. Pollen of the plant of claim 2.

4. An ovule of the plant of claim 2.

5. An *Agrostis palustris* plant having the physiological and morphological characteristics of the plant of claim 2.

6. A tissue culture comprising regenerable cells of the plant of claim 2.

7. An *Agrostis palustris* plant regenerated from the tissue culture of claim 6.

8. A method for producing a first generation parents, ($F_1$) hybrid *Agrostis palustris* seed comprising crossing a plant according to claim 2 with another Agrostis plant.

9. A first generation ($F_1$) hybrid plant produced by growing said hybrid seed of claim 8.

10. Vegetative propagules of the plant of claim 2.

* * * * *